US 7,213,995 B2

United States Patent
Bravo-Loubriel

(10) Patent No.: US 7,213,995 B2
(45) Date of Patent: May 8, 2007

(54) TOOTHBRUSH FOR PREVENTION TREATMENT OF TOOTH SENSITIVITY AND METHOD THEREFOR

(76) Inventor: Michael Bravo-Loubriel, Cond. Granada Park, Apt 236, 100 Marginal St., Guaynabo, PR (US) 00969

( * ) Notice: Subject to any disclaimer, the term of this patent is extended or adjusted under 35 U.S.C. 154(b) by 242 days.

(21) Appl. No.: 10/737,145

(22) Filed: Dec. 15, 2003

(65) Prior Publication Data

US 2005/0129453 A1    Jun. 16, 2005

(51) Int. Cl.
| | |
|---|---|
| A46B 11/02 | (2006.01) |
| A46B 5/02 | (2006.01) |
| A46B 11/04 | (2006.01) |
| B43K 5/12 | (2006.01) |

(52) U.S. Cl. .............. 401/188 R; 401/6; 401/194; 401/270

(58) Field of Classification Search ............ 401/188 R, 401/268, 282, 6, 194, 270; 15/24, 29
See application file for complete search history.

(56) References Cited

U.S. PATENT DOCUMENTS

| | | | | | |
|---|---|---|---|---|---|
| 2,835,912 | A | * | 5/1958 | Pensky ................... | 15/143.1 |
| 2,841,806 | A | * | 7/1958 | Blasi ...................... | 15/24 |
| 3,235,897 | A | * | 2/1966 | Fortenberry ............. | 15/24 |
| 3,903,888 | A | * | 9/1975 | Buelow et al. .......... | 604/186 |
| 4,259,761 | A | * | 4/1981 | Earle ...................... | 15/143.1 |
| 4,519,109 | A | * | 5/1985 | Raymond ................ | 15/110 |
| 5,208,933 | A | * | 5/1993 | Lustig et al. ............ | 15/22.1 |
| 5,301,381 | A | * | 4/1994 | Klupt ...................... | 15/22.1 |
| 5,306,151 | A | * | 4/1994 | Rauch ..................... | 433/216 |
| D421,339 | S | * | 3/2000 | Jeannet et al. .......... | D4/104 |
| 6,331,088 | B2 | * | 12/2001 | Owens .................... | 401/282 |
| 2003/0088932 | A1 | * | 5/2003 | Gardiner ................. | 15/167.1 |
| 2004/0025272 | A1 | * | 2/2004 | Stvartak et al. ......... | 15/143.1 |

* cited by examiner

*Primary Examiner*—David J. Walczak
(74) *Attorney, Agent, or Firm*—Reyes Law Services, PSC; Hector M Rayes Riviera

(57) ABSTRACT

A toothbrush for the treatment of tooth sensitivity is disclosed. The toothbrush disclosed herein incorporates the use of disposable desensitizing agent cartridges thru a pump mechanism.

7 Claims, 1 Drawing Sheet

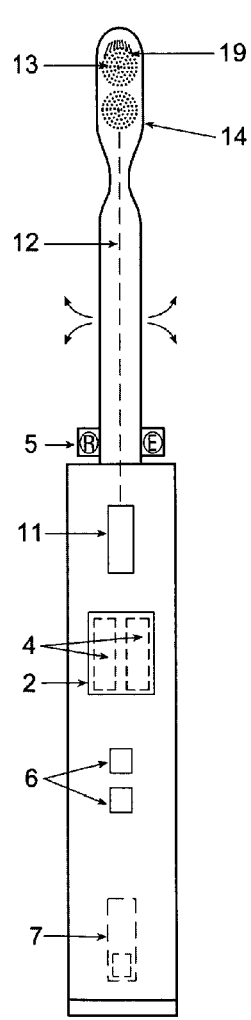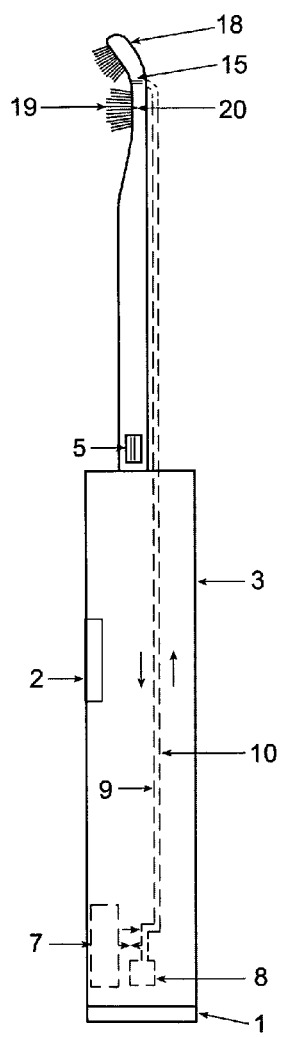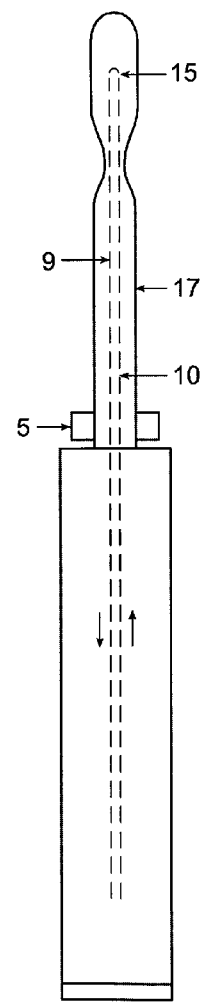

TOOTHBRUSH FOR PREVENTION TREATMENT OF TOOTH SENSITIVITY AND METHOD THEREFOR

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The present invention relates generally to toothbrushes and, more specifically, to a toothbrush for the preventive treatment of tooth sensitivity offering the user the ability to brush his or her teeth in a manner that prevents the ailment of tooth sensitivity.

2. Discussion of the Background

Tooth sensitivity, also known as dentinal sensitivity has been identified as a very common problem among dental patients. Approximately one out of every four adults has one or more sensitive teeth and although once believed to affect mostly older adults, this sensitivity is now being experienced in patients of all ages. It is estimated that at least 45 million Americans suffer at some time from sensitive teeth and 10 million are chronically affected with sensitive teeth. Sensitivity can be described as a short sharp pain triggered by a stimulus such as cold or hot foods/beverages, sweet, sour, or acidic foods and even brushing and flossing.

People at the highest risk of dentinal sensitivity are the aggressive brushers. These people strip the gum tissue away and remove the underlying layer of the tooth root surface (the cementum). Because the cementum is very thin, it doesn't take much pressure to wear away this surface and expose the inner substance, dentin.

Dentin contains numerous tubules (tiny tubes) filled with fluid that extend from the pulp chamber in the center of the tooth to the outer surface of the tooth. The pulp chamber houses the nerves that signal the pain response. So when a stimulus such as cold air or drink comes into contact with the open and exposed tubule on the outside of the tooth, it creates a pressure change in the fluid in the tubules. This pressure change then triggers the nerves in the pulp chamber, resulting in a short, sharp pain response, known as tooth sensitivity.

Although, once developed, patients cannot control sensitivity, they can take proactive steps to decrease or even alleviate the pain. However, there are ways to avoid tooth sensitivity. For instance, having your dentist apply desensitizing agents such as fluoride or varnish, using a desensitizing toothpaste, minimizing use of tartar control toothpastes, minimizing acid food intake—soda-pop, spicy foods etc., controlling clenching/grinding of teeth, not brushing too hard, or using an extra soft toothbrush.

Prevention begins with minimizing the risk of exposing dentinal tubules by brushing gently and using a toothbrush that will be soft on your teeth and gums.

Causes of Tooth Sensitivity

Brushing too hard—Over time, brushing too hard or using a hard-bristled toothbrush may cause excessive wear of your enamel and/or cementum, causing dentin to become exposed.

Gum disease—Inflamed and sore gums may cause sensitivity due to loss of supporting tissues and the resulting exposure of root surfaces.

Gum recession—Movement of the gums away from the tooth due to periodontal disease will expose root surfaces.

Cracked teeth—Chipped or broken teeth may fill with bacteria and plaque resulting in decay and pain.

Grinding your teeth—Grinding or clenching your teeth may wear down the enamel and expose underlying dentin.

Advanced carious lesions close to pulp tissue which is the nerve of the tooth.

Plaque—The presence of plaque on the root surfaces can cause sensitivity.

Effective tooth brushing requires a user to impart a controlled amount of force in applying the toothbrush to the teeth. If too little force is applied, ineffective cleaning results. If excessive force is used, injury to the surface of the gums surrounding the teeth, as well as excessive erosion of the enamel, dentin, and root on the teeth, can result. It has been found that a brushing force, applied normal to the teeth, of 200 to 300 grams is required for effective brushing. Various devices have been designed to teach the proper brushing force to be imparted during tooth brushing in order to obtain effective cleaning without damage. U.S. Pat. No. 4,253,212 ('212) discloses a pressure detection device which may be provided inside or outside of the stem of the toothbrush. U.S. Pat. No. 4,476,604 ('604) and U.S. Pat. No. 4,680,825 ('825) disclose toothbrush holders which sense the amount of force being applied to the toothbrush. Each holder clamps onto and about the toothbrush handle and emits an audio or visual signal when a certain force is applied. The holder is adjustable to permit the users to change their brushing habits by incrementally increasing the applied force until the desired level is reached. The devices disclosed in these prior patents have several drawbacks. The device disclosed in the '212 patent requires a separate training appliance which is attached to a toothbrush handle. This separate add-on training appliance extends the handle to a longer than standard length. This affects the balance of the toothbrush and the user's grip, which can cause variations in brushing force once the training device is removed. Thus, it produces an unnatural instrument. The pressure sensing toothbrush holders disclosed in the '604 and '825 patents are also add-on devices which attach to the toothbrush handles. Additionally, the holders are bulky in comparison to the toothbrush handle itself and require the user to adjust their grip to accommodate the larger holder size. Once again, they produce an unnatural instrument. In addition to the foregoing, U.S. Pat. No. 5,282,291 to Spieler, et al. for a force sensitive handle for hand operated implement discloses an improved handle for a hand operated implement of the type for which it is desirable to control the force of application. The handle has bifurcated sections which are connected by a means for sensing the applied force and indicating a variation of the applied force from a desired level. There are several other toothbrushes in the prior art which try to offer solutions to the problem of tooth sensitivity. For instance, the Philips Sonicare toothbrush has extra-soft, nylon bristles and an extra-wide sweeping motion.

Every dentist has encountered patients with dentin hypersensitivity, either on exposed root or underneath fillings. Advances in research and the development of products have enabled dentistry to better deal with this painful problem.

Fluoride salts have been used for years for desensitization of root surfaces. Forms of fluorides such as sodium fluoride preparations are found in toothpastes such as Prevident 500 Plus® from Colgate®. When used, this fluoride causes the formation of calcium fluoride and other minerals that close the dentinal tubules. A more concentrated sodium fluoride product is the fluoride varnish. This product provides immediate relief for large areas of exposed root surfaces causing hypersensitivity.

Oxalate crystal solutions are another means of mineralizing the dentinal tubule openings. Butler Protect® is an example of a product that causes potassium oxalate to form sealing the tubules. It is available as a toothpaste for patient use or as a solution for professional application.

Other products that are available for professional use include dentinal bonding agents and depolarizing agents. These may be used by dentists if the over-the-counter products fail.

Maintenance of healthy gums is the best way to protect tooth dentin from exposure. The seal made between healthy gums, teeth, and underlying bone provides protection by keeping highly sensitive root surfaces covered.

Proper brushing and flossing are the basis for a good oral care routine. However, overly vigorous brushing, with a hard-bristled toothbrush and/or an abrasive toothpaste may wear tooth enamel and can cause gum recession.

Oral-B® provides a regular, manual sensitive toothbrush and an extra-soft brushhead refill for the Oral-B® range of power toothbrushes. Both brushes have ultra-soft, end rounded bristles that are specially designed to be gentle on sensitive tissue.

In particular, the application of fluoride directly to the sensitive areas of the teeth, is known to be a good desensitizing agent that forms a protective barrier for exposed dentin. There are products, such as Oral-B STOP® Gel, a fluoride gel that is brushed directly onto the affected area with a toothbrush to reduce symptoms.

Fluoridated sealants are one of the many treatments used for prevention of caries and for more advanced sensitivity conditions.

In order to treat sensitive teeth, toothpastes and other dentifrices that include desensitizing agents have been developed for topical treatment of sensitive teeth. For instance, U.S. Pat. No. 5,981,475 to Reynolds discloses an oral composition for the treatment of dentinal hypersensitivity. Table I shows a number of patient applied over-the-counter desensitizing agents.

However, since desensitizing agents only provide temporary relief of painful or sensitive teeth, desensitizing agents applied by the dentist will quickly wear off, leaving the patient with sensitive teeth shortly following the dental visit and long before the next scheduled visit. On the other hand, although a person can use desensitizing toothpaste on a regular basis as part of his or her daily oral hygiene, the time in which a person typically brushes does not provide enough contact time in order to provide the same level of pain relief that is afforded by desensitizing treatments applied by a dentist. A person will typically brush for only one minute or less, which is generally an insufficient amount of time for a desensitizing agent to permeate into the pores and/or fissures within a person's teeth in a high enough concentration in order to desensitize the teeth. Nor are toothpastes able to provide a high enough concentration of desensitizing agent since toothpastes by necessity must include abrasives for cleaning the teeth, surfactants, fluoride, fillers and other agents.

All cited patents and publications on this application are hereby incorporated on by reference on its totality.

Thus, there has been shown and described a toothbrush for the treatment of tooth sensitivity which fulfills all the objects and advantages sought therefor. The invention is not limited to the precise configuration described above. While the invention has been described as having a preferred design, it is understood that many changes, modifications, variations, and other uses and applications of the subject invention will, however, become apparent to those skilled in the art without materially departing from the novel teachings and advantages of this invention after considering this specification together with the accompanying drawings. For example, the particular shapes and proportions of the elements of the toothbrush may be varied as desired. Accordingly, all such changes, modifications, variations and other uses and applications which do not depart from the spirit and scope of the invention are deemed to be covered by this invention as defined in the following claims and their legal equivalents.

TABLE I

Patient-applied Over the Counter desensitizing agents

| Product | Manufacturer | Active Agent | Mechanism of Action |
|---|---|---|---|
| Dental Care ® Sensitive | Arm & Hammer | Potassium nitrate | Blocks nerve repolarization |
| Sensodyne ® Original | Block Drug Company | Potassium* nitrate | Blocks nerve repolarization |
| Sensodyne ® Cool Gel | Block Drug Company | Potassium* nitrate | Blocks nerve repolarization |
| Sensodyne ® Fresh Mint | Block Drug Company | Potassium* nitrate | Blocks nerve repolarization |
| Sensodyne ® Baking Soda | Block Drug Company | Potassium* nitrate | Blocks nerve repolarization |
| Sensodyne ® Tartar + Whitening | Block Drug Company | Potassium* nitrate | Blocks nerve repolarization |
| Sensodyne ® Extra Whitening | Block Drug Company | Potassium* nitrate | Blocks nerve repolarization |
| Colgate ® Sensitive | Colgate-Palmolive Company | Potassium nitrate, stannous fluoride | Blocks nerve repolarization (Dual chamber delivery) |

TABLE I-continued

Patient-applied Over the Counter desensitizing agents

| Product | Manufacturer | Active Agent | Mechanism of Action |
|---|---|---|---|
| Mentadent ® Sensitive | Chesebrough-Ponds Co | Potassium fluoride | Blocks nerve repolarization |
| Crest ® Sensitive | Procter & Gamble | Potassium nitrate | Blocks nerve repolarization |
| Rembrandt Whitening for Sensitive Teeth | Rembrandt | Potassium nitrate | Blocks nerve repolarization |
| AquaFresh ® Sensitive | SmithKline Beecham | Potassium nitrate | Blocks nerve repolarization |

*Care with sodium lauryl sulphate if you are prone to apthous ulcers.
Source: RDH, December 2000. Sensitive Issues by Juliana J. Kim, BSHD, Ms and Iain A. Pretty, BDS, MSc, Volume 20 Issue 12.
The principal active ingredients are:
STRONTIUM CHLORIDE - blocks dental canaliculi to reduce tactile sensitivity or;
POTASSIUM NITRATE - blocks the transmission of sensitive nervous impulses and is more efficient in reducing thermal (heat or cold) and osmotic (sweet and sour) sensitivities
Probe 2001; 35(1):26

Tooth sensitivity can get worse as the patient becomes older unless it is treated in an early stage. Providing a solution to this ailment is difficult because patients usually do not follow instructions or do not understand them. They may also become negligent during brushing of their teeth, and continue to brush their teeth in an incorrect manner. There is also confusion on the part of the patients as to what products to use for this condition. Patients also do not know that they must apply fluoride in a concentrated solution after they finish brushing. The solution has to remain on the teeth for at least 30 minutes after brushing, in order to treat sensitivity correctly.

In sum, in order to treat sensitivity adequately and effectively it is necessary to:

(a) use the right technique for brushing incorporating minimal force and correct angulation to minimize pressure and stress to enamel; and slow bristle movement, with circular motion.

(b) treat the area of the tooth neck with extreme care when brushing.

(c) apply fluoride directly at the tooth neck after brushing.

(d) use of extra soft bristles for brushing.

However, all the aforesaid brushes and methods have not varied in decades and have several areas that could be improved. The available tooth brushes and methods are not mechanized and present several problems.

Therefore, it can be appreciated that there exists a continuing need for a new and improved toothbrush for the preventive treatment of tooth sensitivity, which overcomes these and other deficiencies in the prior art. In this regard, the present invention substantially fulfills this need. The present invention overcomes the inability of prior art to provide a toothbrush for the preventive treatment of tooth sensitivity that takes advantage of the technology developed to date. Various novel toothbrushes and treatment systems have recently been disclosed, yet none provide a more reliable and cost efficient toothbrush and method for the preventive treatment of tooth sensitivity as the toothbrush of the present invention. With the toothbrush of the invention the ailment of tooth sensitivity can be treated effectively once the patient suffers this condition, while also alleviating, controlling, and preventing tooth sensitivity. In addition, the toothbrush of the invention can also contribute to good oral hygiene, the prevention of caries, and gum diseases.

None of the art considered above, taken either simply or in combination teach the use of a lever mechanism to ensure proper brushing technique. In light of the foregoing, it will be appreciated that what is needed in the art is an improved toothbrush and method for treating sensitive teeth that incorporates the teachings of the present invention.

SUMMARY OF THE INVENTION

The object of the present invention is to provide a toothbrush for the treatment of tooth sensitivity.

A further object of the present invention is to provide a mechanism to ensure proper tooth brushing technique.

The toothbrush itself, both as to its construction and its mode of operation will be best understood, and additional objects and advantages thereof will become apparent, by the following detailed description of a preferred embodiment taken in conjunction with the accompanying drawings.

BRIEF DESCRIPTION OF THE DRAWINGS

FIG. 1 is a front view of the toothbrush of the invention;
FIG. 2 is a side view of the toothbrush of the invention;
FIG. 3 is a rear view of the toothbrush of the invention.

DESCRIPTION OF THE PREFERRED EMBODIMENT

Referring now to the drawings, wherein like reference numerals designate the corresponding structure, part, or element, as the case may be, throughout the views, a toothbrush constructed in accordance with the preferred embodiment of the present invention comprises a main cylinder 3, a tube 17 having a head 18, an upper bristle group 13, a lower bristle group 14, wherein each of the upper bristle group and the lower bristle group has shorter bristles 19 in the periphery all around, and a replaceable bristle base 20; wherein said tube comprises a drive shaft 12 for rotating said lower and upper bristles, and said main cylinder further comprises an electric motor 11, an access cover 1 for the insertion of a desensitizing agent cartridge 7, a battery housing 4, having an access cover 2, a miniature pump 8, operational buttons for turning toothbrush on and off and for desensitizing agent application 6, return piping for desensitizing agent 9, dispensing piping for desensitizing agent 10.

Having shorter bristles around the head ensures that the tooth neck will always be treated by this smaller bristles when brushing.

The tube provides support for the bristles and has an angular lever 5 attached to it that brings flexibility plus permits correct angular brushing of every quadrant of the mouth and every surface of teeth. In the preferred embodiment, the desensitizing agent is fluoride. The tube besides allows for pumping of the desensitizing agent to the teeth through an opening 15 in the head that permits this desensitizing agent to be applied correctly. The bristles of different construction and texture will be attached to the tube head by means of a small replaceable bristle base that can be replaced every three months.

In the preferred embodiment, the head 18 of the toothbrush has the contour anatomy of a tooth, creating a tooth profile. It allows treating the upper and lower sections of a sensitive tooth at different areas. In this way, it is able to treat the upper third of the tooth more carefully because this area of the enamel is less dense and more vulnerable to abrasions.

The upper bristles 13 of the toothbrush of the invention are shorter than the lower bristles 14 to prevent damage of the tooth neck, and these bristles are of extra soft texture. The lower bristles 14 are longer than the upper bristles 13, but still soft in texture and they will treat the other two thirds or coronal portion of teeth. Another specific component of the bristle design is that the outer periphery of both bristle zone areas will always be composed of bristles that are shorter in length; therefore avoiding any stress to the tooth neck region on every surface of teeth, and on every quadrant of the mouth.

The bristles rotate in oscillating patterns, clockwise and counter clockwise. In the preferred embodiment, said rotation is circular, but in other embodiments semi-circular rotation is possible. The design velocity of the rotation is very slow since this is crucial in preventing tooth abrasions.

The toothbrush is provided with disposable cartridges 7 that can be inserted at the base of the cylinder. The cylinder has a button that starts a pump mechanism that pumps the desensitizing agent through the tube up to the head where the desensitizing agent is released via an opening 15 in the middle of the bristle zones. In this way, the desensitizing agent is dispensed directly into the tooth neck where it is mostly needed. This is done after brushing.

The tube has a 45 degree color-coded angular lever. This color-coded lever makes the tube rotate when it is pressed during brushing. This will assure correct brushing technique at the perfect angle therefore causing less stress to the tooth enamel.

The method for brushing is as follows:
1. When brushing on the left side, the first color side of the lever points up while the second colored side points down.
2. Thus, by pressing the first colored side, the upper teeth will be brushed at a 45 degree angle, and by pressing the second colored side, the lower teeth will be brushed at a 45 degree angle also.
3. This method may be used for the left side cheek area and right side tongue area.

When brushing on the right side the method is the opposite.
1. The second colored side of the lever points up and the first colored side points down.
2. The lever is pressed on the second colored side for brushing teeth at the 45 degree angle, and pressed on the first colored side for brushing teeth at this angle also.
3. This method is used for right side cheek area and left side tongue area.

The advantage of this color coded manual lever is that at a 45 degree angle technique of brushing will always be exerted correctly on every quadrant, and surface of the mouth.

This correct technique of brushing plus the circular oscillating pattern, and slow velocity will ensure perfect brushing every time.

The toothbrush of the invention comprises: a specific bristle design to treat the tooth neck with more caution, a lever attachment that will always create a 45 degree angle, and makes the tube rotate therefore incorporating correct brushing technique on every surface and quadrant of the mouth. Less stress will be applied on the teeth by using the method and the lever, circular oscillating pattern and slow velocity, a disposable desensitizing solution cartridge and a pump mechanism to release the desensitizing solution through an outlet to the region of the tooth neck. This is a crucial step to control sensitivity.

The color coded 45 degree angular lever which provides rotation to the tube, and the disposable desensitizing agent cartridge, a pump mechanism, smaller bristles around all the periphery, and an outlet for the release of the tooth desensitizing solution.

In the preferred embodiment, the preferred desensitizing agent is fluoride. Another possible alternative for the desensitizing agent is potassium nitrate at 5% concentration and/or fluoride salts.

Another alternative for the oscillation could be semicircular motion.

Thus, there has been shown and described a toothbrush for the treatment of tooth sensitivity which fulfills all the objects and advantages sought therefor. The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. For example, the particular shapes and proportions of the elements of the toothbrush may be varied as desired. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

What is claimed is:

1. A toothbrush for the prevention and treatment of tooth sensitivity, comprising:
   a) main cylinder having a tube attached to one of the extremes of the said cylinder;
   b) a head attached to the extreme of the said tube and located substantially in at the opposite side wherein the cylinder is attached to the said tube;
   c) a manual color-code lever having a first colored side and a second colored side attached to the said tube;
   d) at least two bristle groups, one in the upper side of the said head and other in the lower side of the said head; wherein the upper bristle group has first inner bristles and first outer bristle and wherein the lower bristle group has a second inner bristles and second outer bristles;

wherein the said upper bristles are shorter in length than the said lower bristles and;

wherein said first outer bristles are shorter in length than the said first inner bristles and;

wherein said second outer bristles are shorter in length than said second inner bristles and;

wherein the said head comprises a desensitizing agent outlet and said main cylinder contains a disposable desensitizing agent cartridge.

2. The toothbrush of claim 1, wherein the said tube further comprises a drive shaft for rotating said lower and upper bristles.

3. The toothbrush of claim 2, wherein said desensitizing agent is selected from the group consisting of potassium nitrate and/or fluoride salts.

4. The toothbrush of claim 3, wherein the said main cylinder further comprises an electric motor to power the said shaft, a first access cover for the insertion of the said cartridge, a battery housing having a second access cover to provide power to the electric motor, operational buttons, for turning toothbrush on and off and for desensitizing agent application, return piping for desensitizing agent, and dispensing piping for desensitizing agent.

5. A method for preventing and treating tooth sensitivity by brushing teeth using the toothbrush of claim 1 comprising the steps of:

a) brushing on one side of the mouth, while the first colored side of the lever points up while the second colored side points down, whereby by pressing the first colored side, the upper teeth will be brushed at 45 degrees angle, and by pressing the second colored side, the lower teeth will be brushed at 45 degrees angle;

(b) brushing the cheek area of the said mouth side of (a) and the opposite tongue area of the said selected mouth side;

(c) brushing the opposite side of the mouth of the selected side in step (a); while keeping the second colored side of the lever pointing up and the first colored side pointing down;

(d) brushing the upper teeth at a 45 degrees angle while keeping the second colored side pointing up and the first colored side pointing down; brushing the lower teeth at an angle of 45 degrees while keeping the first colored side pointing up and the second colored side down;

(e) brushing the cheek area of the same mouth side of (c) and the opposite tongue area of the said selected mouth side.

6. The method of claim 5, wherein the side of the mouth in step (a) is the left side and the side of the mouth in step (c) is the right side.

7. The method of claim 5, wherein the side of the mouth in step (a) is the right side and the side of the mouth in step (c) is the left side.

* * * * *

UNITED STATES PATENT AND TRADEMARK OFFICE
CERTIFICATE OF CORRECTION

PATENT NO. : 7,213,995 B2
APPLICATION NO. : 10/737145
DATED : May 8, 2007
INVENTOR(S) : Michael Bravo-Loubriel Page 1 of 1

It is certified that error appears in the above-identified patent and that said Letters Patent is hereby corrected as shown below:

On Title Page item 74, correction of the attorney's name is requested. The name of the attrorney should read --Reyes Law Services, PSC; Hector M. Rayes Riviera--.

Signed and Sealed this

Twenty-eighth Day of August, 2007

JON W. DUDAS
*Director of the United States Patent and Trademark Office*